(12) United States Patent
Aoki et al.

(10) Patent No.: US 8,142,761 B2
(45) Date of Patent: Mar. 27, 2012

(54) METHOD OF PREDICTING SPOT FORMATION ON THE SKIN USING SPOT SITE-ACCELERATING GENES AS AN INDICATOR THEREOF AND METHOD OF SCREENING INHIBITORS OF SPOT FORMATION ON THE SKIN

(75) Inventors: Hirofumi Aoki, Yokohama (JP); Jiro Kishimoto, Yokohama (JP); Osamu Moro, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 546 days.

(21) Appl. No.: 12/226,656

(22) PCT Filed: Apr. 24, 2007

(86) PCT No.: PCT/JP2007/059341
§ 371 (c)(1),
(2), (4) Date: Oct. 24, 2008

(87) PCT Pub. No.: WO2007/126104
PCT Pub. Date: Nov. 8, 2007

(65) Prior Publication Data
US 2009/0123401 A1    May 14, 2009

(30) Foreign Application Priority Data
Apr. 25, 2006 (JP) ................................. 2006-120479

(51) Int. Cl.
*A61K 49/00* (2006.01)

(52) U.S. Cl. ......... 424/9.2; 424/1.11; 424/1.65; 424/9.1
(58) Field of Classification Search ................. 424/1.11, 424/1.65, 1.69, 9.1, 9.2
See application file for complete search history.

(56) References Cited

FOREIGN PATENT DOCUMENTS
| WO | WO 02/29058 A2 | 4/2002 |
| WO | WO 2005/033710 A1 | 4/2005 |
| WO | WO 2006/002433 A2 | 1/2006 |

OTHER PUBLICATIONS

Curto et al., "Biomarkers of Human Skin Cells Identified Using DermArray DNA Arrays and New Bioinformatics Methods," Biochemical and Biophysical Communications, 2002, 291(4):1052-1064.

Goto et al., "A New Melanoma Antigen Fatty Acid-Binding Protein 7, Involved in Proliferation and Invasion, Is a Potential Target for Immunotherapy and Molecular Target Therapy," Cancer Research, Apr. 15, 2006, 66(8):4443-4449.

*Primary Examiner* — D L Jones
(74) *Attorney, Agent, or Firm* — Foley & Lardner LLP

(57) ABSTRACT

The present invention provides a skin test method for predicting the formation of spots in the skin. This method is characterized by judging skin to be susceptible to spot formation in the case expression of genes consisting of MLSTD1, MOGAT1, FADS2, FADS1, HSD3B1, ELOVL3, BG1, PECR, FABP7, FA2H, HAO2, ALOX15B, PDE6A, LZTS1, SEC14L4, BAMBI, CIDEA, TERE1, GAL, THRSP, INSIG1 or CUTL2 in the epidermis is accelerated, or the expression of genes consisting of RBBP6, MSMB, WIF1, ANKRD12, FLG, SYNE2, SCEL, NKTR or AMBP in the epidermis is decreased as compared with normal expression in the epidermis.

2 Claims, 3 Drawing Sheets

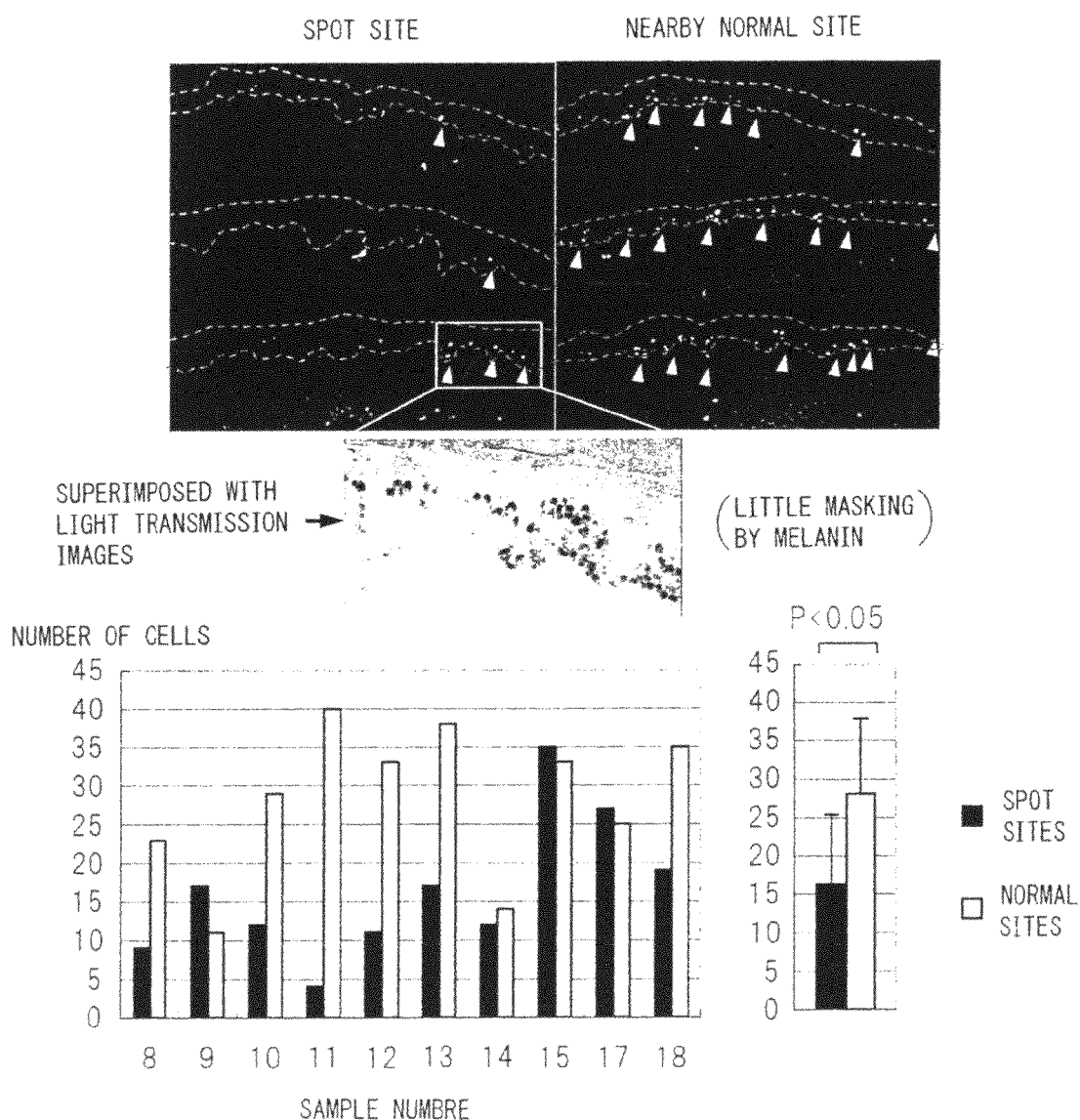

METHOD OF PREDICTING SPOT FORMATION ON THE SKIN USING SPOT SITE-ACCELERATING GENES AS AN INDICATOR THEREOF AND METHOD OF SCREENING INHIBITORS OF SPOT FORMATION ON THE SKIN

CROSS-REFERENCE TO RELATED APPLICATIONS

This application is a National Stage application of PCT/JP2007/059341, filed Apr. 24, 2007, which claims priority from Japanese patent application JP 2006-120479, filed Apr. 25, 2006.

TECHNICAL FIELD

The present invention relates to a skin test method for predicting the formation of spots in the skin.

BACKGROUND ART

When the action of the enzyme tyrosinase within melanocytes (pigment-forming cells) is activated abnormally due to ultraviolet rays, hormonal imbalance or psychological stress and so forth, formation of melanin pigment is enhanced and they are successively sent out to surrounding epidermal cells. If the rate at which melanin pigment is produced is excessively fast and turnover is no longer normal due to the effects of ultraviolet rays and so forth, the melanin pigment is unable to be excreted to the outside and remains in the skin, and this is believed to result in the formation of spots in the skin.

Once a spot has been formed, it is preferably to treat the spot as quickly as possible, and a visual sensory evaluation of the spot by a beautician, or an early assessment of the presence of a spot by a quantitative evaluation of the spot using equipment such as an apparatus for capturing images of skin condition or a calorimeter, is desired for the purpose of providing treatment (Japanese Unexamined Patent Publication No. 2003-144393).

Once a spot being formed, it is not easily removed, and treatment is required that improves skin metabolism to quickly expel the unnecessary melanin and prevent excess melanin from being formed. Thus, it is preferably to care for the skin prior to the formation of a spot. However, since there are individual differences in susceptibility to spot formation and there are various conditions that cause their formation, it is typically difficult to predict the formation of a skin spot. Accordingly, a means for predicting whether or not the skin is susceptible to spot formation prior to formation thereof would be extremely effective as a preventive measure.

There is a report describing an attempt to evaluate the ease of formation of skin spots by collecting samples from sites of normal epidermis and using as an indicator thereof the detection of NT-3, ADAM9 or HB-EGF at each site (Japanese Unexamined Patent Publication No. 2003-245097). In addition, there is also a report describing an attempt to prevent the formation of skin spots by inhibiting c-KIT and ET (Japanese Unexamined Patent Publication No. 2004-83551). However, in addition to the complex pathological reactions in the body involved in the formation of skin spots not being completely understood, under the present circumstances in which a plurality of pigment synthesis stimulation pathways are known, there is still concern as to whether a definitive solution can be achieved in the case of judging the formation of skin spots or treating it by only focusing on a small number of genes. Therefore, a report has been published describing the detection of variations in a wide range of genes and using those genes as indicators for diagnosis (Japanese Unexamined Patent Publication No. 2004-205246). However, this report describes the detection of genes varying due to exposure of the skin to sunlight using a method referred to as SAGE, thus resulting in the need for the establishment of diagnostic and accommodation methods based on a wide-ranging analysis of skin spots per se.

Therefore, we determined a chronic inflammatory state characteristic of the sites of skin spots by comparing spot sites and normal sites of skin spot model mice using a microarray (Japanese Unexamined Patent Publication Nos. 2005-106475 and 2005-110505). The inventors of the present invention have now found acceleration of sebaceous gland-associated genes and inhibition of cornification-associated genes at spot sites in addition to the characteristic described above by comparing sites of age spots with normal sites, which are one of the typical skin spots found in humans.

DISCLOSURE OF THE INVENTION

In consideration of the aforementioned problems, the inventors of the present invention conducted extensive studies on whether it is possible to provide a means for predicting whether or not the skin is susceptible to spot formation before a spot is formed in the skin. As a result of a microarray analysis of RNA from the epidermis and dermal upper layer of 11 cases of age spot sites and control sites, the inventors of the present invention found that expression of the genes indicated below was accelerated or inhibited at age spot sites. Thus, it was clearly found that skin can be judged to be susceptible to the formation of skin spots by examining the expression of the following genes in human skin.

TABLE 1(1)

| | | | Expression | |
|---|---|---|---|---|
| Gene ID | Gene Name | Function | Level | Ratio |
| NM_018999 | Male sterility domain containing 1 (MLSTD1); Fatty acyl CoA reductase 2 | Conversion of fatty acids to long-chain alcohols; present in peroxisomes and sebaceous glands | 485 | 2.37 |
| BC039181 | Diacylglycerol 0-acyltransferase 2-like 3 | Synthesis of trigylcerides; decreased psoriasis; expressed in sebaceous glands | 534 | 2.02 |
| NM_058165 | Monoacylglycerol 0-acyltransferase 1 (MOGAT1) | Addition of fatty acids to monoglycerides; wax synthesis | 374 | 2.14 |

Lipid-Associated Accelerating Genes

TABLE 1(1)-continued

Lipid-Associated Accelerating Genes

| Gene ID | Gene Name | Function | Expression Level | Ratio |
|---|---|---|---|---|
| NM_004265 | Fatty acid desaturase 2 (FADS2) | Synthesis of fatty acids or arachidonic acid; expressed in epidermis and sebaceous glands | 21594 | 2.66 |
| NM_013402 | Fatty acid desaturase 1 (FADS1) | Synthesis of fatty acids or arachidonic acid | 3830 | 2.34 |
| NM_000862 | Hydroxy-delta-5-steroid dehydrogenase, 3-beta-andosteroid delta-isomerase (HSD3B1) | Synthesis of steroid hormones; expressed in adrenals, testes, ovaries and sebaceous glands | 847 | 2.07 |
| NM_152310 | Very long chain fatty acid elongation-like 3 (ELOVL3) | Expressed in sebaceous glands and hair follicles | 1346 | 1.94 |
| NM_015016 | Lipidosin (BG1) | Synthesis of acyl-CoA | 2289 | 1.95 |
| NM_018441 | Peroxysomal trans-2-enoyl-CoA reductase (PECR) | Beta-oxidation enzyme | 400 | 1.80 |
| NM_001446 | Fatty acid binding protein 7, brain (FABP7) | Transport of free fatty acids to mitochondria | 1856 | 2.09 |
| NM_02430 | Fatty acid 2-hydroxylase (FA2H) | Metabolism of fatty acids | 2165 | 1.94 |
| NM_016527 | Hydroxyacid oxidase 2 (long chain) (HAO2) | Metabolism during alpha-oxidation; present in peroxisomes | 228 | 2.11 |
| BC035217 | Arachidonate 15-lipoxygenase, second type (ALOX15B) | Synthesis of lipoxin from arachidonic acid | 5180 | 2.08 |

TABLE 2(2)

Information Transfer-Associated Accelerating Genes

| Gene ID | Gene Name | Function | Expression Level | Ratio |
|---|---|---|---|---|
| NM_000440 | Phosphodiesterase 6A, cGMP-specific, rod, alpha (PDE6A) | Relates to photoreceptors | 542 | 3.41 |
| NM_021020 | Leucine zipper putative tumor suppressor 1 (LZTS1) | Transcription factor; tumor suppression | 1488 | 2.04 |
| NM_174977 | SEC14-like (*S. cerevisiae*) (SEC14L4) | Inhibition of PL$_3$ kinase | 658 | 1.91 |
| NM_012342 | BMP and activin membrane-bound inhibitor homolog (*Xenopus laevis*) (BAMBI) | Inhibition of TGFb signaling | 704 | 2.18 |
| NM_001279 | Cell death- inducing DFFA-like effector (CIDEA), transcription product | Activation of apoptosis | 1968 | 1.92 |
| NM_013319 | Transitional epithelial response protein (TERE1) | Tumor suppression | 1352 | 1.85 |
| NM_015973 | Galanin (GAL) | Neuropeptide; suppression of inflammation | 17159 | 2.58 |
| BC031989 | Thyroid hormone- responsive protein (SPOT14 homolog, rat) (THRSP) | Regulation of lipid synthesis | 11297 | 2.38 |
| NM_005542 | Insulin induced gene 1 (INSIG1), transcription product mutant 1 | Regulation of lipid synthesis and carbohydrate metabolism | 1718 | 2.30 |
| AB006631 | Cut-like 2 (*Drosophila*) (CUTL2) | Transcription factor | 206 | 2.26 |

TABLE 3(3)

Suppressed Expression Gene Group

| Gene ID | Gene Name | Function | Expression Level | Ratio |
|---|---|---|---|---|
| NM_006910 | Retinoblastoma binding protein 6 (RBBP6) | Cell cycle | 1694 | 0.54 |
| NM_002443 | Microsemino- protein, beta (MSMB), transcription product mutant PSP94 | Signaling | 1093 | 0.49 |

TABLE 3(3)-continued

Suppressed Expression Gene Group

| Gene ID | Gene Name | Function | Expression Level | Ratio |
|---|---|---|---|---|
| NM_007191 | WNT inhibitory factor 1 (WIF1) | Signaling | 1790 | 0.54 |
| AK024808 | Ankyrin repeat domain 12 (ANKRD12) | Keratin construction | 538 | 0.54 |
| M60502 | Human profilaggrin | Keratin construction | 28020 | 0.54 |
| L01090 | Human profilaggrin (FLG) gene exon 1-3 | Keratin construction | 8764 | 0.44 |
| AK095241 | Spectrin repeat containing, nuclear envelope 2 (SYNE2), transcription product mutant 1 | Binding of actin | 907 | 0.54 |
| NM_144777 | Sciellin (SCEL), transcription product mutant 2 | CE-associated | 9262 | 0.52 |
| AF273047 | *Homo sapiens* CTCL tumor antigen se20- | Tumor marker | 1018 | 0.35 |
| NM_005385 | Natural killer tumor recognition sequence (NKTR) | Tumor marker | 337 | 0.55 |
| NM_001633 | Alpha-1-microglobulin/bikunin precursor (AMBP) | Blood-associated | 223 | 0.50 |

There are no reports describing a correlation with skin pigment for any of the above genes. Thus, it is extremely surprising that the expression of these genes is accelerated or inhibited in association with skin spots.

In a first aspect thereof, the present invention provides a skin test method for predicting the formation of spots. This method is characterized in that the skin is judged to be susceptible to the formation of spots in the case the expression of a sebaceous gland-associated gene is accelerated in the epidermis in comparison with normal expression in the epidermis. Here, spots refer to light brown to deep brown flat spots appearing in the skin. Spots mentioned with respect to spot model mice primarily indicate age spots.

In a preferred embodiment, those sebaceous gland-associated genes for which expression in the epidermis is accelerated are genes encoding protein selected from the group of genes indicated in Table 1.

In a second aspect thereof, the present invention provides a skin test method for predicting the formation of spots in the skin, comprising: judging skin to be susceptible to the formation of skin spots in the case expression of a gene encoding protein selected from the group of genes indicated in Table 2 in the epidermis is accelerated as compared with normal expression in the epidermis.

In a third aspect thereof, the present invention provides a skin test method for predicting the formation of spots in the skin, comprising: judging skin to be susceptible to the formation of skin spots in the case expression of the genes indicated in Table 3 in the epidermis is decreased as compared with normal expression in the epidermis.

In a preferred embodiment, variations in the expression of the genes in the epidermis are determined by measuring the amount of the protein in the epidermis.

More preferably, the measurement is carried out by ELISA or RIA using an antibody specific to the protein.

In another preferred embodiment, variations in the expression of the genes in the epidermis are determined by measuring the amount of mRNA encoding the proteins extracted from the epidermis. Preferably, measurement of the mRNA is carried out by a polymerase chain reaction.

In a fourth aspect thereof, the present invention provides a method of screening a spot formation inhibitory factor and/or spot removal factor, comprising: evaluating a candidate compound for the ability to inhibit or accelerate expression of the gene and/or activity of a gene product thereof in the form of a protein, and selecting an inhibitor or activator having that inhibitory or accelerative ability as a spot formation inhibitory factor and/or spot removal factor.

In a preferred embodiment, this method comprises the application of the inhibitor or activator having the inhibitory or accelerative ability to a skin model, and selecting a drug having skin spot formation inhibition and/or skin spot removal effects.

In a fifth aspect thereof, the present invention provides a whitening method, method of suppressing the formation of spots in the skin or method for removing spots in the skin by inhibiting acceleration of the expression of genes encoding protein selected from the group of genes consisting of MLSTD1, MOGAT1, FADS2, FADS1, HSD3B1, ELOVL3, BG1, PECR, FABP7, FA2H, HAO2 and ALOX15B.

According to the present invention, a skin test method can be provided for predicting the formation of spots in the skin.

BRIEF DESCRIPTION OF THE DRAWINGS

FIG. 4 shows a comparison of the number of growing cells. More specifically, this drawing shows the comparison results of the numbers of dividing cells at sites of skin spots and nearby normal sites using Ki-67 antibody that specifically stains cells during the mitotic phase. The photographs show three examples of fluorescent immunostaining, which clarifies that the number of positive cells is small at the sites of skin spots. A combined photograph superimposing light transmission images on the results of fluorescent immunostaining is shown to indicate that the fluorescence is not masked by melanin. Moreover, the numbers of positive cells per 1 mm of tissue were counted and summarized in the graph. The average numbers thereof indicate that the number of growing cells is significantly smaller at the sites of skin spots.

BEST MODE FOR CARRYING OUT THE INVENTION

Figure 1:
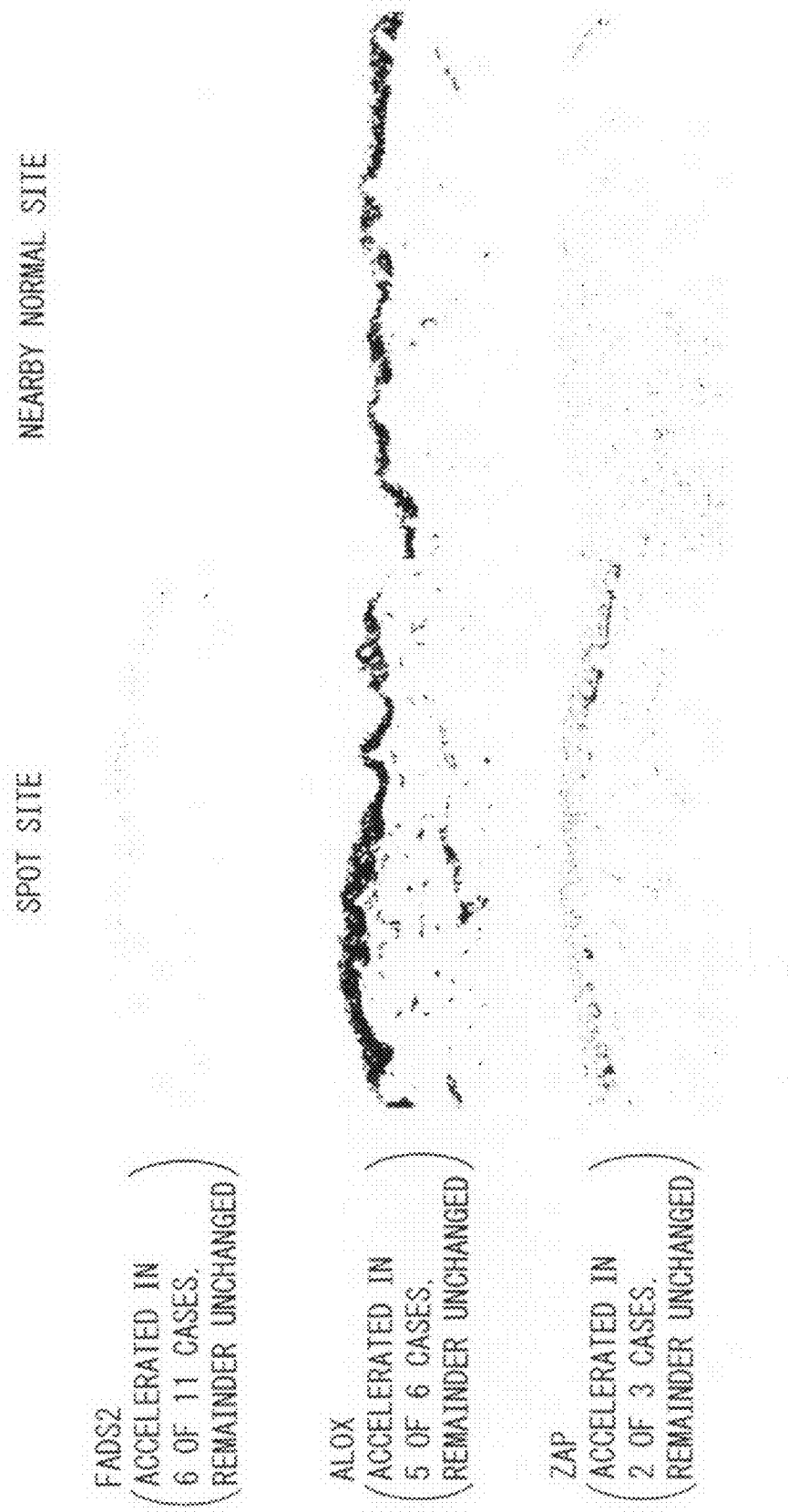
FIG. 1 shows the results of the distribution of differential expression of lipid-associated genes between spot sites and nearby normal sites as determined by in situ hybridization. The blue color at areas indicated by white arrows indicates an epidermal site where a signal was detected. Each gene demonstrated that its expression is prone to be accelerated in epidermis at the sites of skin spots.

As has been previously described, there are no reports describing a correlation with skin pigment for any of the above genes. As a result of a microarray analysis of RNA from the epidermis and dermal upper layer of 11 cases of age spot sites and control sites, the inventors of the present invention found that expression of the genes indicated below was accelerated or inhibited at age spot sites. Thus, it was surmised that the formation of skin spots can be predicted by using these genes as indicators.

Skin Test Method for Predicting Spot Formation

The present invention provides a skin test method for predicting the formation of spots in skin, and preferably human skin. This method is characterized by judging skin to be susceptible to the formation of skin spots in the case expression of genes selected from the group consisting of genes indicated in Tables 1, 2 and 3 in a target epidermis is accelerated or decreased as compared with normal expression in the epidermis. The evaluation criterion may be, for example, judging skin to be susceptible to spot formation if the expression of the aforementioned genes in the epidermis is accelerated by at least 10%, at least 20%, at least 30%, at least 50%, at least 70% or at least 100% in comparison with the expression of those genes in a control epidermis.

The skin to be tested may be, for example, skin of the face, neck, limbs or any other portion of the skin that is susceptible to the formation of spots or for which there is concern over the formation of spots. The normal epidermis that is free of spot formation, namely the control epidermis, may include normal areas in the vicinity of skin spots of the same individual that is, for example, not likely to be exposed to ultraviolet rays, or epidermis at a site that is relatively resistant to the formation of skin spots such as the abdomen or thigh. Samples may be collected from the epidermis in accordance with established methods corresponding to the epidermis to be detected and type of detection method, and samples are preferably collected by biopsy.

Acceleration or inhibition of expression of the aforementioned genes in the epidermis is determined by, for example, measuring the amount of protein encoded by said genes in the epidermis. Preferably, this measurement uses a specific antibody to the aforementioned protein, and can be carried out by various known methods in the industry, such as immunostaining methods using fluorescent substances, pigments or enzymes, Western blotting or immunoassay methods such as ELISA and RIA. In addition, increases in expression can also be determined by extracting RNA from the epidermis and measuring the amount of mRNA that encodes the gene. Extraction of mRNA and measurement of the amount thereof are carried out by known methods in the industry, and for example, quantification of RNA is carried out by the quantitative polymerase chain reaction (PCR) method.

Expression in the epidermis of a polynucleotide capable of hybridizing under highly stringent conditions to the aforementioned genes can be determined by extracting RNA from the epidermis and measuring the amount of mRNA corresponding to the polynucleotide. Extraction of mRNA and measurement of an amount thereof are known in the industry, and for example, quantification of RNA is carried out by a quantitative polymerase chain reaction (PCR) method.

As has been previously described, the present invention is based on the finding that expression of the aforementioned genes is specifically accelerated or inhibited in the epidermis at the site of a skin spot as compared with a site not having a skin spot as a result of analyzing skin RNA from the site of a skin spot and a site not having a skin spot using a microarray. Thus, it is surmised that a medicament could be developed that inhibits the formation of spots and/or removes formed spots by using as an indicator inhibition of the expression of the above genes in the epidermis and/or the activity of gene products thereof in the form of the aforementioned proteins.

Thus, the present invention provides a pharmaceutical or skin external composition comprising an inhibitor for inhibiting expression of the aforementioned genes as a spot formation inhibitory factor and/or spot removal factor. The composition as claimed in the present invention is able to prevent the formation or remove spots in the skin.

The pharmaceutical or skin external composition of the present invention is applied in the form of, for example, an aqueous solution, oily liquid, other type of solution, milky liquid, cream, gel, suspension, microcapsules, powder, granules, capsules or solid preparation. After preparing in these forms using conventionally known methods, they can be applied, attached, sprayed, injection, consumed or inserted into the body in the form of a lotion, milky lotion, cream, ointment, salve, poultice, aerosol, water-oil two-layer system, water-oil-powder three-layer system, injection, oral preparation (e.g., tablets, powders, granules, pills, syrup, lozenges) or suppositories. The aforementioned inhibitor can be contained in this composition at, for example, 0.001 mM to 1 M, preferably 0.01 to 100 mM and more preferably 0.1 to 10 mM, based on the total amount of the composition with any particular limitations as a spot formation inhibitory factor and/or spot removal factor.

Among these dosage forms, lotions, milky lotions, creams, ointments, salves, poultices, aerosols and other skin external preparations are suitable for the object of the present invention. Furthermore, the skin external preparations listed here include prescription pharmaceuticals, over-the-counter pharmaceuticals (such as ointments) and cosmetics (such as facial washes, milky liquids, creams, gels, essences (beauty washes), facial packs, facial masks and other basic cosmetics, foundations, lipstick and other makeup cosmetics, as well as oral cavity cosmetics, fragrant cosmetics, hair cosmetics and body cosmetics). The pharmaceutical or skin external preparation of the present invention is particularly suitably applied as a spot preventive cosmetic.

Conventionally known vehicles and fragrances as well as oils, surfactants, antiseptics, metal ion chelating agents, water-soluble polymers, thickeners, pigments and other powdered components, ultraviolet protectors, moisturizers, antioxidants, pH regulators, cleansers, desiccants or emulsifiers and so forth are suitably incorporated in a pharmaceutical or skin external preparation of the present invention corresponding to the desired drug form. Moreover, other pharmacologically active components can be incorporated into a pharmaceutical or skin external preparation of the present invention within a range that does not impair the expected effects as a result of incorporation.

Screening Method for Spot Formation Inhibitory Factor and/or Spot Removal Factor The present invention additionally provides a method for screening for a spot formation inhibitory factor and/or spot removal factor. This method is characterized by evaluating a candidate compound for the ability to inhibit or accelerate expression of the aforementioned genes and/or activity of gene products thereof in the form of proteins, and selecting an inhibitor having that inhibitory ability as a skin spot formation inhibitor and/or spot removal factor.

In a preferred embodiment, the screening method further comprises applying an inhibitor or activator having the inhibitory or accelerative ability to a skin model, and selecting an inhibitor of activator that has skin spot formation inhibitory and/or skin spot removal effects.

A step for confirming skin spot formation inhibitory and/or skin spot removal effects of the aforementioned inhibitor or activator can be carried out by applying the inhibitor or activator to a skin model using, for example, skin cell monolayer culturing, co-culturing, three-dimensional culturing or skin spot model mice (Japanese Patent Application No. 2003-343549). In a preferred embodiment, a solution such as an aqueous solution of the inhibitor or activator is prepared followed by repeatedly applying to the skin of a spot model animal and evaluating the formation of spots in the skin to judge the presence or absence of the aforementioned effects.

The following provides a more detailed explanation of the present invention by indicating a specific example thereof. Furthermore, the present invention is not limited thereto Sampling of Age Spots Age spots, which had been identified as age spots by a dermatologist, were selected from the backs of 16 male volunteers age 40 and over who had given their informed consent, and collected by biopsy of the epidermis and dermal upper layer to a depth of 3 mm under local anesthesia. Collection of skin spots was carried out in accordance with the guidelines of the Shiseido Ethics Committee.

Collection of RNA from Skin

Skin fragments collected from the age spots and surrounding normal areas and the buttocks serving as a control were frozen and homogenized followed by extraction of RNA using ISOGEN (Nippon Gene Co., Ltd., using the recommended protocol of the manufacturer) and purifying with RNeasy (Qiagen). The RNA was electrophoresed with a bioanalyzer (Agilent Technologies) to confirm quality and purity.

Reaction of Microarray Samples

Sample preparation and hybridization were carried out in compliance with the recommended protocol of Agilent Technologies. Labeled cRNA was synthesized using a Low RNA Input Linear Amplification & Labeling Kit (Agilent Technologies). After purifying with RNeasy (Qiagen, using the recommended protocol of the manufacturer), the cDNA was hybridized with a whole human genome oligoarray (Agilent Technologies, G4112A) followed by washing and reading the data with a scanner manufactured by Agilent Technologies.

Analysis Results

As a result of comprehensively analyzing the expression of about 40,000 types of genes, in addition to acceleration of melanocyte-associated genes, the results were characterized by acceleration of inflammatory genes in comparison with unexposed control areas on the buttocks of 9 subjects. This comparison of skin spots/unexposed areas was equivalent to an analysis in skin spot model mice, and the results coincided therewith. Next, in a comparison of 11 cases of normal areas near age spots, the results were characterized by accelerated expression of lipid-associated genes and information transfer-associated genes as shown in Tables 1 and 2 for each type of accelerating gene such as melanocyte-associated genes and inflammatory genes, as well as suppression of a group of genes including horny layer-associated genes as shown in Table 3.

In situ hybridization was carried out to investigate the distribution of expression of lipid-associated accelerating genes in the skin (FIG. 1). Lipid-associated genes consisting of FADS2, ALOX and ZAP128 that were found to be accelerated based on microarray analysis were observed to be expressed in the skin and were confirmed to demonstrate that its expression is prone to be accelerated at sites of spots in the skin.

Figure 2:
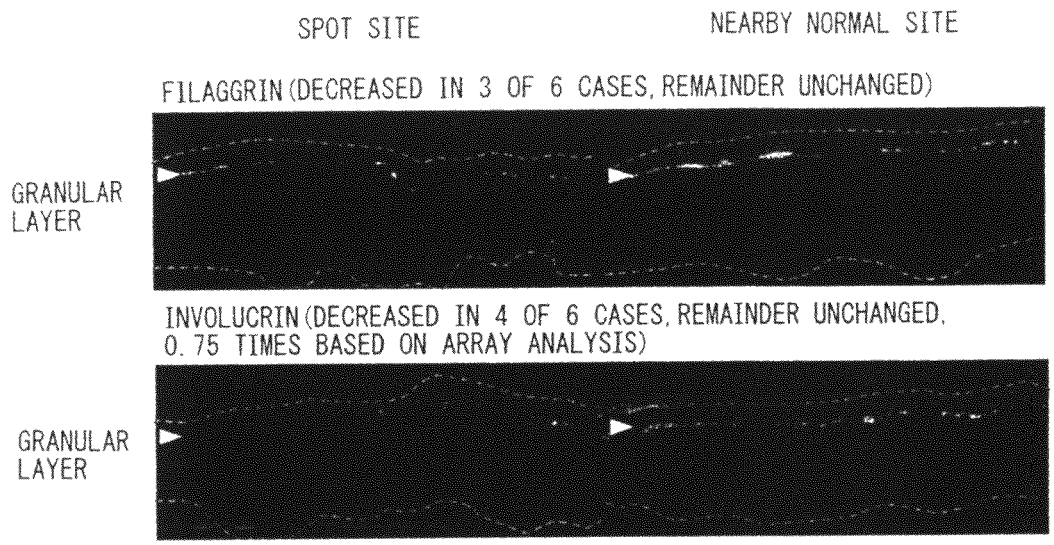
FIG. 2 shows the results of the distribution of differential expression of proteins constituting horny layer between spot sites and nearby normal sites as determined by fluorescent immunostaining. The green color at areas indicated by white arrows indicates sites in the granular layer where a signal was detected. Each gene demonstrated that its expression is prone to be decreased in epidermis at the sites of skin spots.

Among proteins constituting horny layer, which accounted for a large number of genes for which expression was decreased, the distribution of the expression of filaggrin and involucrin, which are expressed in the granular layer, in the skin was investigated by immunostaining (FIG. 2). A decreasing tendency was confirmed for the expression of these proteins at sites of spots in the skin.

Figure 3:
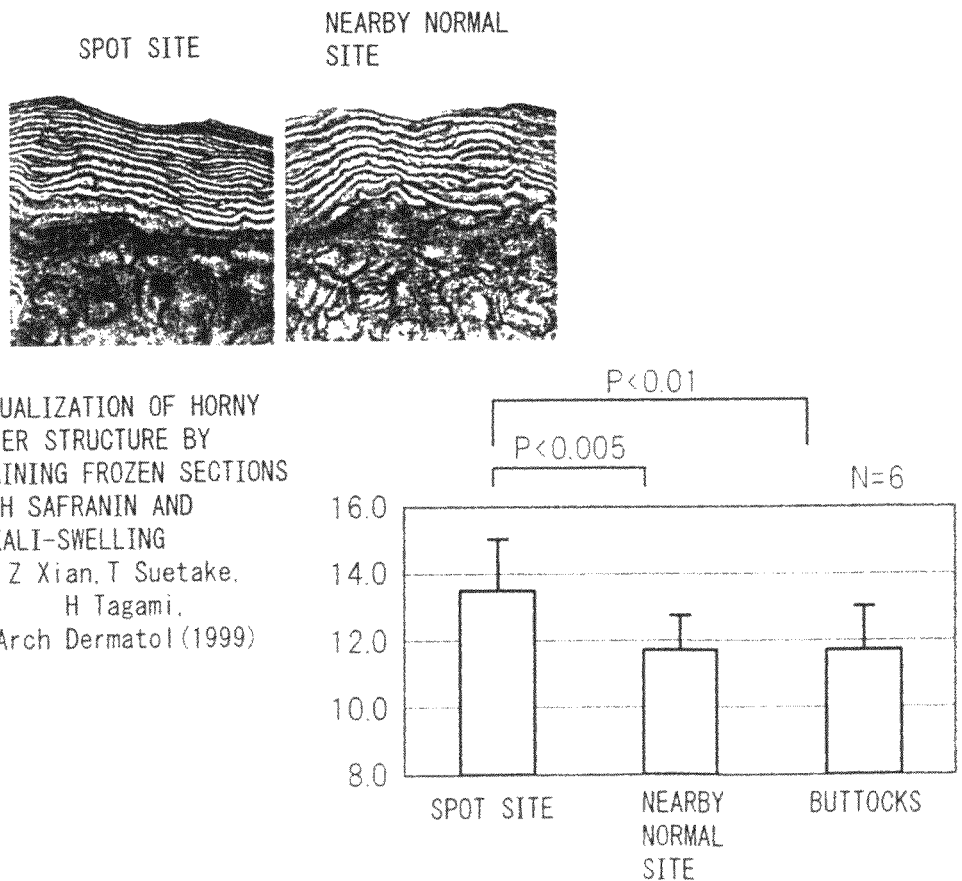
FIG. 3 shows the results of counting the number of horny layers visualized by swelling with base after having stained horny layers for comparing the number of horny layers with safranin stain. The photographs show one example of this comparison. The average values of the number of horny layers in six samples at four locations each are shown in the graph. The number of horny layers can be seen to be larger at sites of skin spots as compared with nearby normal sites.

Since the horny layer itself is predicted to change as a result of a decrease in proteins constituting horny layer, the number of horny layers was counted by visualization thereof (FIG. 3). As a result, the number of horny layers was shown to be large at sites of spots in the skin. This indicates a decrease in horny layer exfoliation. A decrease in differentiation of keratinocytes was suggested based on the decreases in proteins constituting horny layer and horny layer exfoliation.

Therefore, when an attempt was made to examine keratinocyte proliferation (FIG. 4), there were clearly confirmed to be fewer growing cells in the basal layer at sites of spots in the skin. These were thought to consist nearly entirely of basal layer keratinocytes. In other words, as a result of the occurrence of decreased keratinocyte proliferation and decreased horny layer formation and exfoliation, there was thought to be a decrease in turnover. In addition, excessive acceleration of lipid-associated genes occurred at sites of skin spots in the skin, thereby suggesting the occurrence of abnormal keratinocyte differentiation. In addition to this situation, there was also stimulation of melanocytes due to a chronic inflammatory trend that was characteristic of exposed sites, and this was thought to lead to the formation of pigment deposition due to the occurrence of melanin stagnation due to excess production of melanin and decreased melanin turnover.

The invention claimed is:

1. A method of predicting the formation of spots on skin, comprising:
    (a) determining the amount of expression of a gene encoding a protein selected from the group consisting of MLSTD1, MOGAT1, FADS2, FADS1, HSD3B1, ELOVL3, BG1, PECR, FA2H, HAO2 and ALOX15B in the epidermis; and
    (b) comparing the amount of gene expression from step (a) to that of normal gene expression in the epidermis; wherein if the gene expression in step (a) is greater than the normal gene expression, the subject is susceptible to spot formation.

2. The method according to claim 1, wherein the increased expression of the genes in the epidermis is determined by extracting mRNA encoding the protein from the epidermis.

* * * * *